United States Patent
Marseille et al.

(10) Patent No.: US 12,427,236 B2
(45) Date of Patent: Sep. 30, 2025

(54) GAS EXCHANGE UNIT, METHOD FOR PRODUCING A GAS EXCHANGE UNIT AND KIT WITH A GAS EXCHANGE UNIT AND A HUMIDIFYING AND HEATING DEVICE

(71) Applicant: Hemovent GmbH, Aachen (DE)

(72) Inventors: Oliver Marseille, Aachen (DE); Bernhard Schmitz, Schleiden (DE)

(73) Assignee: Hemovent GmbH, Aachen (DE)

( * ) Notice: Subject to any disclaimer, the term of this patent is extended or adjusted under 35 U.S.C. 154(b) by 1424 days.

(21) Appl. No.: 16/308,505

(22) PCT Filed: Jun. 12, 2017

(86) PCT No.: PCT/EP2017/000685
§ 371 (c)(1),
(2) Date: Dec. 10, 2018

(87) PCT Pub. No.: WO2017/211460
PCT Pub. Date: Dec. 14, 2017

(65) Prior Publication Data
US 2019/0160217 A1   May 30, 2019

(30) Foreign Application Priority Data

Jun. 10, 2016  (DE) .......................... 102016007105.2
Aug. 30, 2016  (DE) .......................... 102016010398.1

(51) Int. Cl.
*A61M 1/16*  (2006.01)
*A61M 1/36*  (2006.01)
(Continued)

(52) U.S. Cl.
CPC ........ *A61M 1/1698* (2013.01); *A61M 1/3623* (2022.05); *B01D 63/025* (2013.01);
(Continued)

(58) Field of Classification Search
CPC ............ A61M 1/1698; A61M 2206/10; A61M 60/113; A61M 60/38; A61M 1/26;
(Continued)

(56) References Cited

U.S. PATENT DOCUMENTS 5,964,725 A * 10/1999  Sato ....................... B01D 71/76
                                                        604/4.01
6,454,999 B1   9/2002  Farhangnia et al.
(Continued)

FOREIGN PATENT DOCUMENTS

CN   103491993 A    1/2014
DE   19532365 A1    3/1997
(Continued)

OTHER PUBLICATIONS

English language machine translation of JP2010-213851, 7 pages, No Date.*
(Continued)

*Primary Examiner* — Pranav N Patel
(74) *Attorney, Agent, or Firm* — Michael J. Brown

(57) ABSTRACT

The present invention relates to a gas exchange unit for use in extracorporeal membrane oxygenation (ECMO) or extracorporeal live support (ECLS) according to a method for producing such a gas exchange unit as well as a kit with a gas exchange unit and a humidifying and heating device.

26 Claims, 13 Drawing Sheets

(51) Int. Cl.
*B01D 63/02* (2006.01)
*B01D 53/22* (2006.01)

(52) U.S. Cl.
CPC ....... *B01D 63/026* (2013.01); *A61M 2206/10* (2013.01); *B01D 2053/224* (2013.01); *B01D 2257/504* (2013.01); *B01D 2259/4533* (2013.01); *B01D 2317/025* (2013.01); *B01D 2317/04* (2013.01); *B01D 2317/06* (2013.01); *B01D 2319/025* (2013.01); *B01D 2319/04* (2013.01); *B01D 2319/06* (2013.01)

(58) Field of Classification Search
CPC ...... A61M 2206/16; A61M 2205/3331; A61M 2206/20; A61M 2205/7536; A61M 2205/3341; B01D 63/02; B01D 63/025; B01D 63/026; B01D 2053/224; B01D 2257/504; B01D 2259/4533; B01D 2317/025; B01D 2317/04; B01D 2317/06; B01D 2319/025; B01D 2319/04; B01D 2319/06; B01D 2313/08; B01D 2313/10; B01D 69/08; B01D 2313/105; B01D 2313/20; B01D 2321/2016; B01D 2313/025; B01D 2313/19; B01D 2313/208; B01D 2313/26
See application file for complete search history.

(56) References Cited

U.S. PATENT DOCUMENTS

| | | | | |
|---|---|---|---|---|
| 2002/0057989 | A1* | 5/2002 | Afzal | A61M 1/267 604/6.14 |
| 2002/0143397 | A1* | 10/2002 | von Segesser | A61M 1/1625 128/205.28 |
| 2010/0106072 | A1 | 4/2010 | Kashefi-Khorasani et al. | |
| 2014/0030146 | A1* | 1/2014 | Takeuchi | B01D 63/02 422/46 |
| 2014/0227134 | A1* | 8/2014 | Joost | A61M 1/16 210/85 |
| 2015/0129493 | A1* | 5/2015 | Federspiel | B01D 69/08 210/651 |
| 2017/0258978 | A1* | 9/2017 | Bartlett | A61M 1/1698 |
| 2018/0117231 | A1* | 5/2018 | Matheis | B01D 63/043 |
| 2018/0133388 | A1* | 5/2018 | Mazzoli | A61M 1/1698 |

FOREIGN PATENT DOCUMENTS

| | | |
|---|---|---|
| DE | 60031706 T2 | 9/2007 |
| DE | 102011052188 A1 | 1/2013 |
| GB | 2533027 A | 6/2016 |
| JP | S61143075 A | 6/1986 |
| JP | H04193178 A | 7/1992 |
| JP | 2001079083 A | 3/2001 |
| JP | 2010213851 A | 9/2010 |
| WO | WO-9952621 A1 | 10/1999 |
| WO | WO-2014183852 A1 | 11/2014 |
| WO | WO-2017211460 A1 | 12/2017 |

OTHER PUBLICATIONS

English language machine translation of JP2001-079083A, 7 pages, No Date.*
CN 201780045093.1 Office Action dated Jan. 28, 2021.
JP2019-517139 Translation of Office Action dated Jan. 27, 2021.
PCT/EP2017-000685 Search Report & Written Opinion dated Dec. 14, 2017.

* cited by examiner

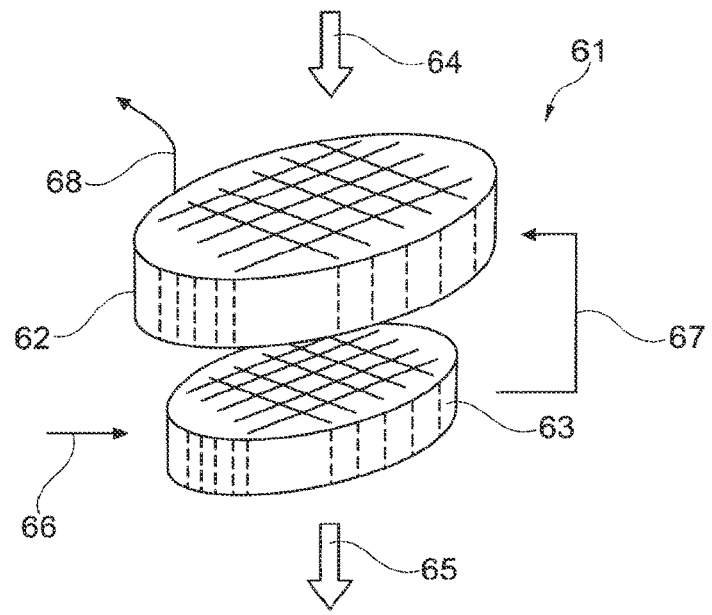
Fig. 6
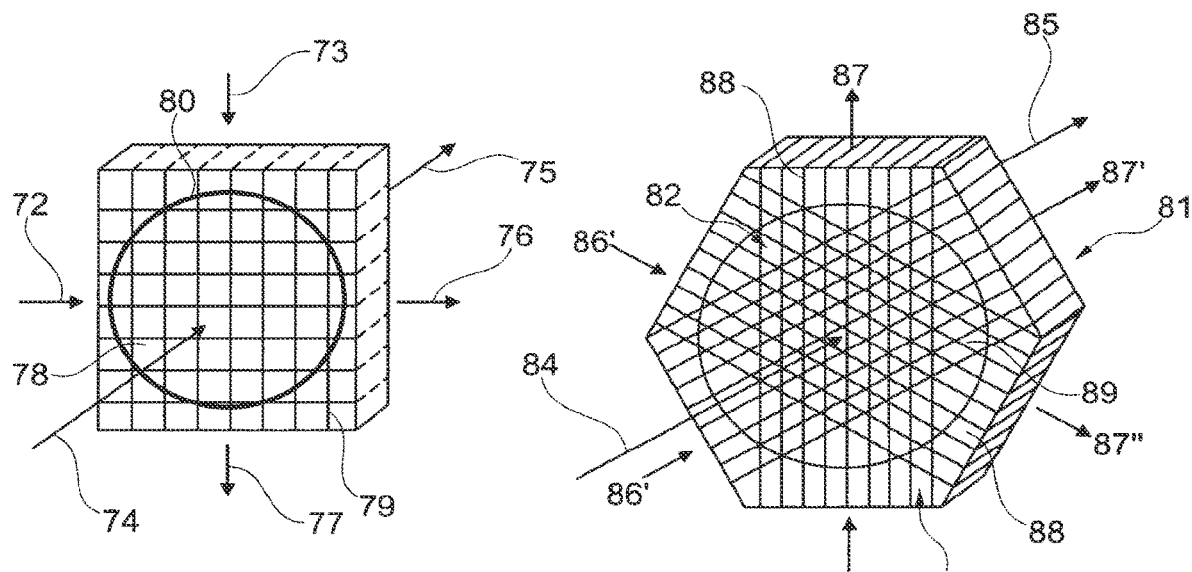
Fig. 7a
Fig. 7b

GAS EXCHANGE UNIT, METHOD FOR PRODUCING A GAS EXCHANGE UNIT AND KIT WITH A GAS EXCHANGE UNIT AND A HUMIDIFYING AND HEATING DEVICE

The present invention relates to a gas exchange unit for use in extracorporeal membrane oxygenation (ECMO) or extracorporeal life support (ECLS), and a method for producing such a gas exchange unit as well as a kit with a gas exchange unit and a heating device.

Heart-lung machines replace the vital circulatory functions of blood delivery and gas exchange (O2 input and CO2 removal from the blood) during cardiac surgery. By inference, heart-lung machines can also be used to stabilise patients with heart or lung insufficiency over a period of days. This is called extracorporeal membrane oxygenation (ECMO) or extracorporeal live support (ECLS).

The ECMO oxygenators currently in use are based on the design of oxygenators as used in cardiac surgery. As a rule, the solely open-pore membrane fibres are replaced by membranes with closed diffusion membranes. Against this background the specifications and design are based on the requirements of cardiac surgery.

The object of the present invention is to improve the oxygenators known from prior art, in particular for ECMO and ECLS applications.

This is achieved by a gas exchange unit with a hollow-fibre module, wherein the gas exchanger characteristics of the hollow-fibre module is adaptable. Thus, when the requirements relating to the gas exchanger characteristics change, these can be adapted as needed before or during operation. In particular, an adaptation can take place during production. The hollow-fibre module may in particular be a fibreboard.

By an adaptation of the gas exchanger characteristics of a gas exchange unit is meant the change in CO2 removal and/or in O2 input or the change in the ratio of the two values to one other. This can be achieved in different ways.

By an adaptation of the gas exchanger characteristics is meant in particular a change in the effective surface area or effective fibre length. For example, a change in the effective fibre length may be achieved by the in-line or in-series connection of the fibres. Thus, for example, it may be advantageous to provide a long effective fibre length by counter-current charging, as in this way oxygen consumption can be reduced.

An adaptation of the gas exchange characteristics can also be performed by changing the flow rate of the gas in the fibres of the hollow-fibre module. This gas flow rate can be adjusted from the outside by a pressure gradient. Along the length of the fibre the concentration gradient for CO2 decreases, i.e. the transfer of CO2 decreases in accordance with Fick's first law. But if the flow rate is increased this effect is weakened, i.e. CO2 transfer is increased. This, however, has a negative impact on the amount of oxygen to be used.

Here it is advantageous if a hollow-fibre module can be completely or partially connected to or disconnected from the gas flow. In this way the gas exchanger characteristics within a hollow-fibre module can be adjusted by changing the effective surface area.

In this case it is particularly advantageous if the gas exchange unit has a shutter on the gas side, in particular a slide valve and/or a rotary slide valve and/or throttle, wherein the shutter being arranged so that fibre regions cannot be connected in a flow-through manner.

It can also be advantageous if fibre regions of the hollow-fibre module can be differently charged with gas. This results in different amounts and compositions of gas being able to flow through the fibre regions subject to the blood-side gas transfer requirement (CO2 and O2), and thus the oxygen consumption can also be reduced.

It is further advantageous if the gas exchange unit provides an overflow channel device. This allows the different charging of the fibre regions by means of differing pressure gradients. The overflow channel device may provide a plurality of chambers connected by overflow channels. Such a device may, in particular, be attached on both side surfaces on which the gas flows into the hollow-fibre module.

It is advantageous if the overflow channel device has adjustable overflow channels. This means that the flow pattern in the overflow channel device can be adjusted and hence be adapted to different usage states of the gas exchange unit. This may be performed, for example, by a slide valve provided on an adjustment device.

It is also advantageous if the hollow-fibre module has a cover. This enables the pneumatic resistance to be increased on the side surface on which the gas flows in. One or more covers may be attached. In this way the differing loading of the fibre regions of the hollow-fibre module can also be achieved.

It is, moreover, advantageous for the cover to have a pneumatic resistance gradient, differing thickness or differing materials (differing porosity). This also allows continuous transitions in charging, in which case the range boundaries become blurred.

It is further advantageous and independently inventive if a gas-side humidifying and heating device is located upstream of the hollow-fibre module. This means that the gas can be heated before entering the hollow-fibre module. The gas is thus saturated with water vapour and has a temperature above blood temperature. In the hollow-fibre module the gas gives off heat and a part of the water vapour condenses and releases the condensation energy to the blood. The condensate can be collected underneath the heat exchanger.

The hollow-fibre module may be drum-shaped. This permits a space-saving design and provides advantages in production.

In a drum-shaped arrangement it is advantageous if the diameter-to-length ratio of the hollow-fibre module>1.5 (is greater than 1.5). This results in shorter fibres for the same effective surface area. The partial pressure drop of the oxygen is reduced on the inside, and so the oxygenator becomes more effective than conventional products in terms of the CO2 transfer rate.

It is also advantageous if in the hollow-fibre module a blood-impermeable layer is spirally arranged from the inside to the outside. The blood flow is thus guided in a certain direction, allowing the flow path to be controlled. The flow path can, in particular, be extended in this way. Here the blood flow can be guided outwards from the inside or inwards from the outside or diagonally outwards or inwards. This has the advantage of making various geometric arrangements possible.

It may be advantageous for the gas exchange unit to have two or more hollow-fibre modules. By this means the gas exchanger characteristics can be adjusted before or during operation of the gas exchange unit by altering the effective surface area in the individual hollow-fibre modules. Where there are several hollow-fibre modules this is especially possible due to the differing arrangement of the hollow-fibre modules. Long-term stability, blood compatibility and performance can thus be improved against the background of a diverging indication in ECMO and ECLS.

It may further be advantageous if the hollow-fibre module can be differently charged with gas. By this means different amounts and compositions of gas can flow through the different hollow-fibre modules subject to the blood-side gas transfer requirement ($CO_2$ and $O_2$), and the oxygen consumption can thus also be reduced.

It is further advantageous if the gas exchange unit has an overflow channel device. This means that different charging of the hollow-fibre modules can be performed by different pressure gradients. The overflow channel device may have a plurality of chambers connected by overflow channels. Such a device may, in particular, be attached to both side surfaces on which the gas flows into the hollow-fibre modules.

It is particularly advantageous if the hollow fibre modules are connected to one or more valves. By this, the flow direction of the individual hollow-fibre modules can be controlled by the valve. The gas transfer rates can thus be adjusted to the clinical indications, allowing the $CO_2$ elimination rate and $O_2$ input to be set separately by interconnecting the modules or connecting them in parallel.

The effective gas exchanger surface area can also be reduced or extended as required during therapy.

In this way it is also possible to introduce other therapeutically effective gases by charging individual hollow-fibre modules with them.

It is particularly advantageous if the hollow-fibre modules in the gas flow can be connected in parallel or in series. The gas exchanger characteristics can thus be changed by the different connection only. It is possible to regulate whether new unused gas or gas which has already passed through gas exchange is used for another hollow-fibre module. It is also possible to charge the hollow-fibre modules specifically with different gas compositions ($O_2$, $CO_2$ and $O_2$, $O_2$ and NO etc.). It is possible, in particular, to charge different hollow-fibre modules with different gas compositions.

The hollow-fibre modules may also be drum-shaped and arranged concentrically inside each other. Here the blood can be guided outwards from the inside or inwards from the outside or diagonally outwards. In this design it is also possible for a blood-impermeable layer to be spirally arranged from inside to outside in the hollow-fibre modules. This allows the blood to be directed spirally from inside to outside or from outside to inside. One, two or more channels are possible here.

Another advantage is for the hollow-fibre modules to be formed as fibre mats and arranged one behind the other in the blood flow. A plurality of hollow-fibre modules can therefore be connected to a gas exchange unit in a stacked arrangement. The hollow-fibre modules thus connected can be appropriately differently interconnected and so combined with each other and charged with gas.

It is advantageous if the fibre direction of a fibre mat is arranged at an angle to the fibre direction of a second fibre mat. This is particularly advantageous if the angle is between 10° and 170°, in particular 120°. Crossing can also improve the gas exchanger characteristics and blood guidance.

It is further advantageous if the diameter-to-length ratio of the hollow-fibre modules is less than 1. This also results in shorter fibres with the aforementioned advantages for the same effective surface area.

A second independently inventive aspect of the invention is for the gas exchange unit to have a heating element. This heating element may be electric. It is further advantageous if this is provided on the gas side in the gas exchange unit. It may be provided in a housing. Heat can thus be introduced into the blood and water condensation can be prevented.

It is advantageous if the heating element is arranged on the gas inlet side in order to heat the gas prior to the exchange procedure with the blood.

The heating element may be of rod-form or plate-form design. It is also possible for the heating element to be implemented by a wire wound onto a support structure or bent in a meandering manner.

It is advantageous if the heating element provides structures to increase the exchange area between heating element and gas. These may comprise ribs or plates around which the gas is guided. Plates may have drill holes through which the gas flows. It is also conceivable for the gas to be guided through externally heated channels.

It is also advantageous for two or more heating elements to be arranged on the gas side, one behind the other or in parallel.

It is also advantageous for a rod-form or plate-form heating element to be inserted into the gas exchange unit from outside and be reused on another gas exchange unit after use.

A third independently inventive aspect of the invention is that the embedding material can form a cylindrical closure towards the blood side. This results in a homogenous flow distribution which has low shear stresses and good washout and is therefore particularly blood-friendly.

A fourth independent aspect of the invention relates to a method for producing a gas exchange unit, in which the embedding of the fibres can be carried out in a single production step in a centrifuge.

It is advantageous if, in a first step, the automated production of a hollow-fibre module can be performed from one or more fibre mats. Modular production can then be performed from several hollow-fibre modules in a second step by combining and potting the gas exchange units with different effective surface area and effective fibre length. These may then additionally be completely or partially activated before use, on commissioning or during operation, or charged with gas by using a different connection.

A fifth independent aspect of the invention relates to a kit with a gas exchange unit according to the invention and a humidifying and heating device, wherein the humidifying and heating device of the gas exchange unit is connected upstream in the gas flow.

The invention will be explained in more detail below with the aid of the drawings, in which FIG. 1 is a schematic representation of a gas exchange unit with two hollow-fibre modules connected in series;

Figure 5A:
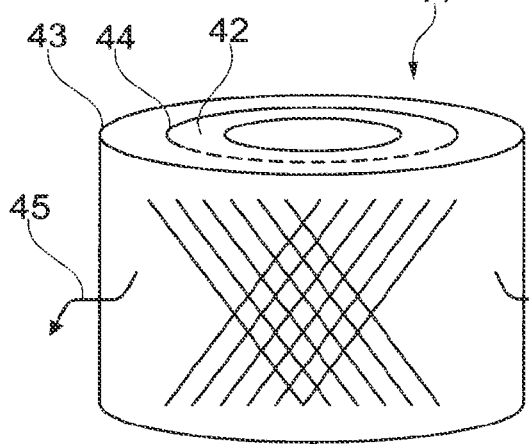
Figure 5B:
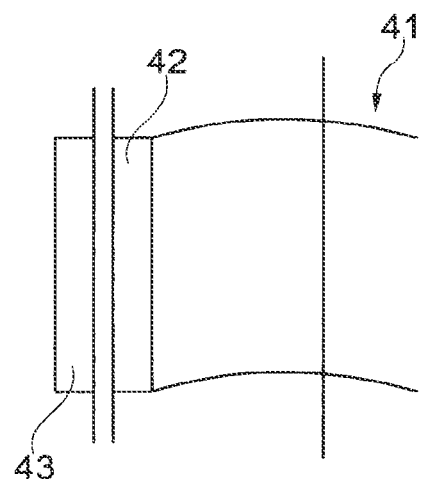
Figure 5C:
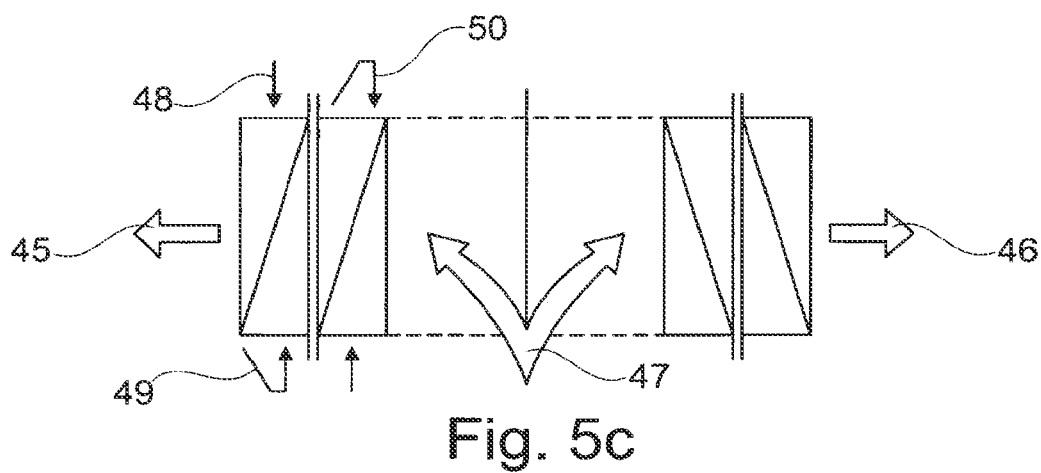
Figure 8A:
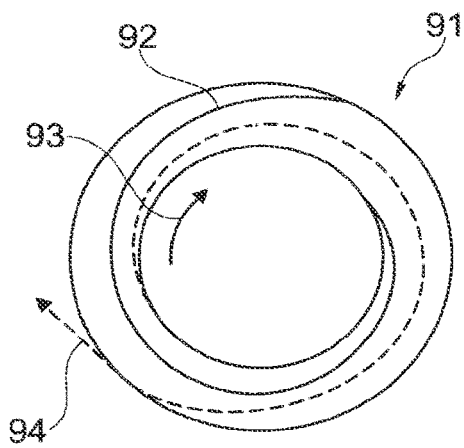
Figure 8B:
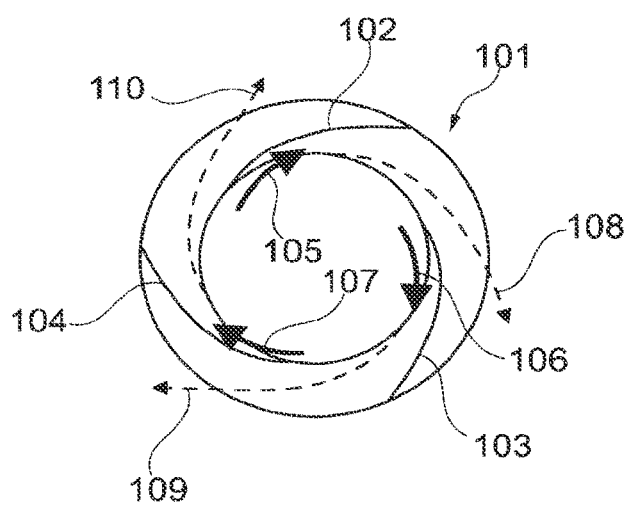
Figure 9A:
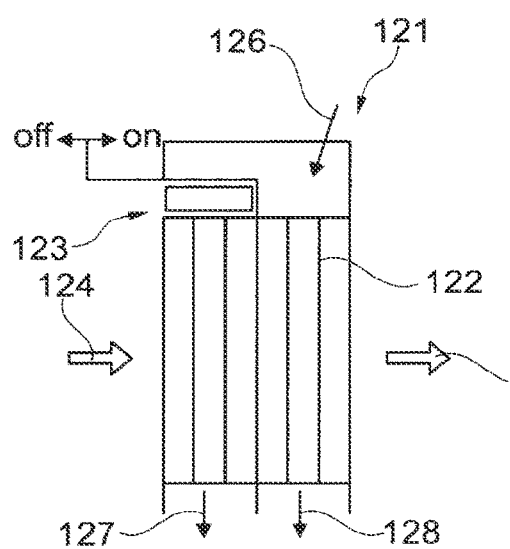
Figure 9B:
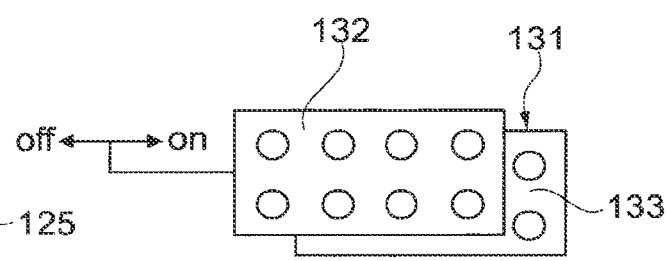
Figure 10:
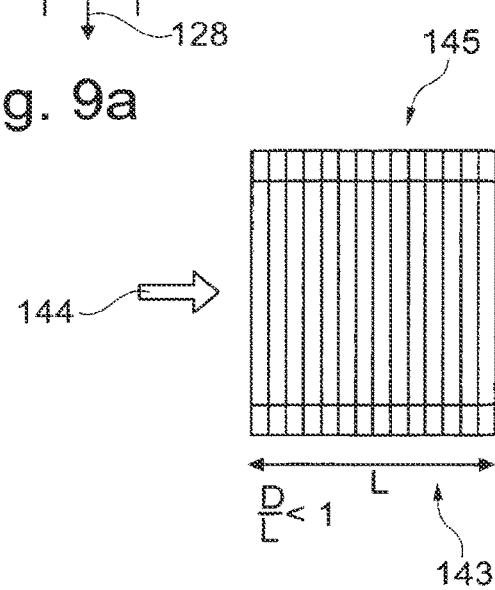
Figure 11:
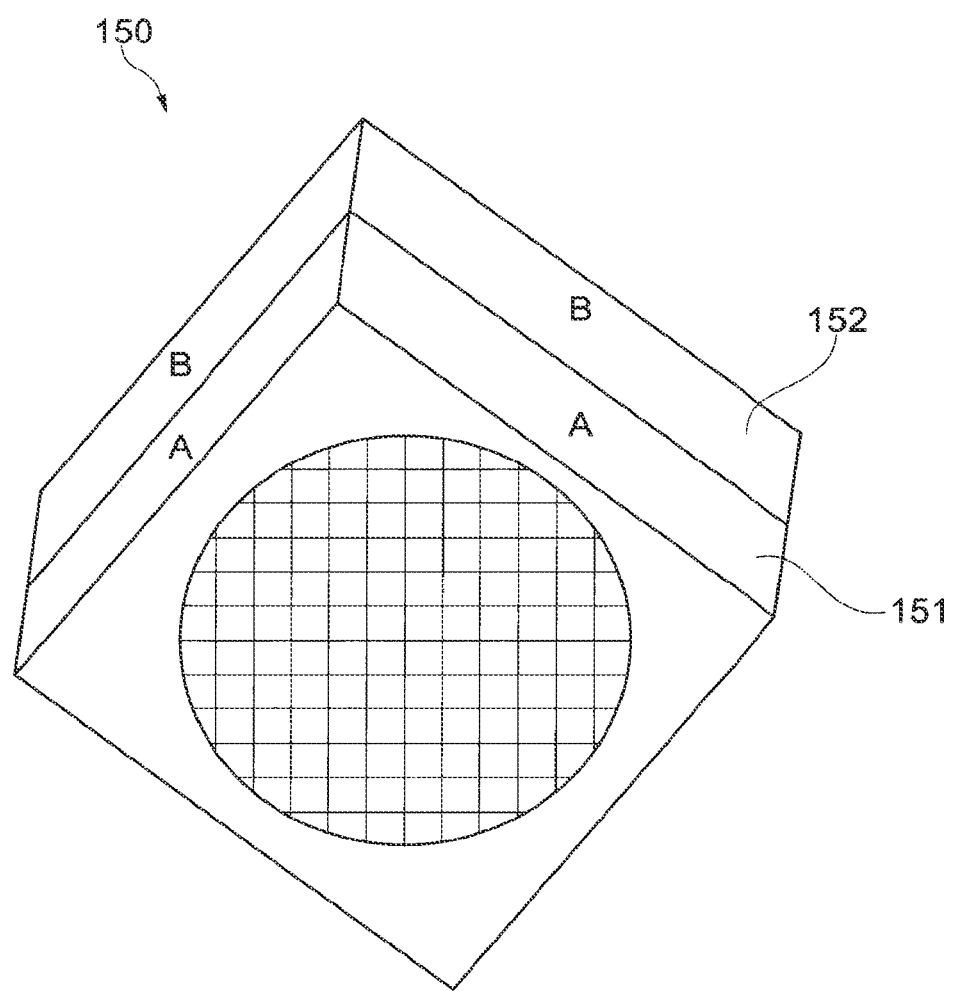
Figure 12:
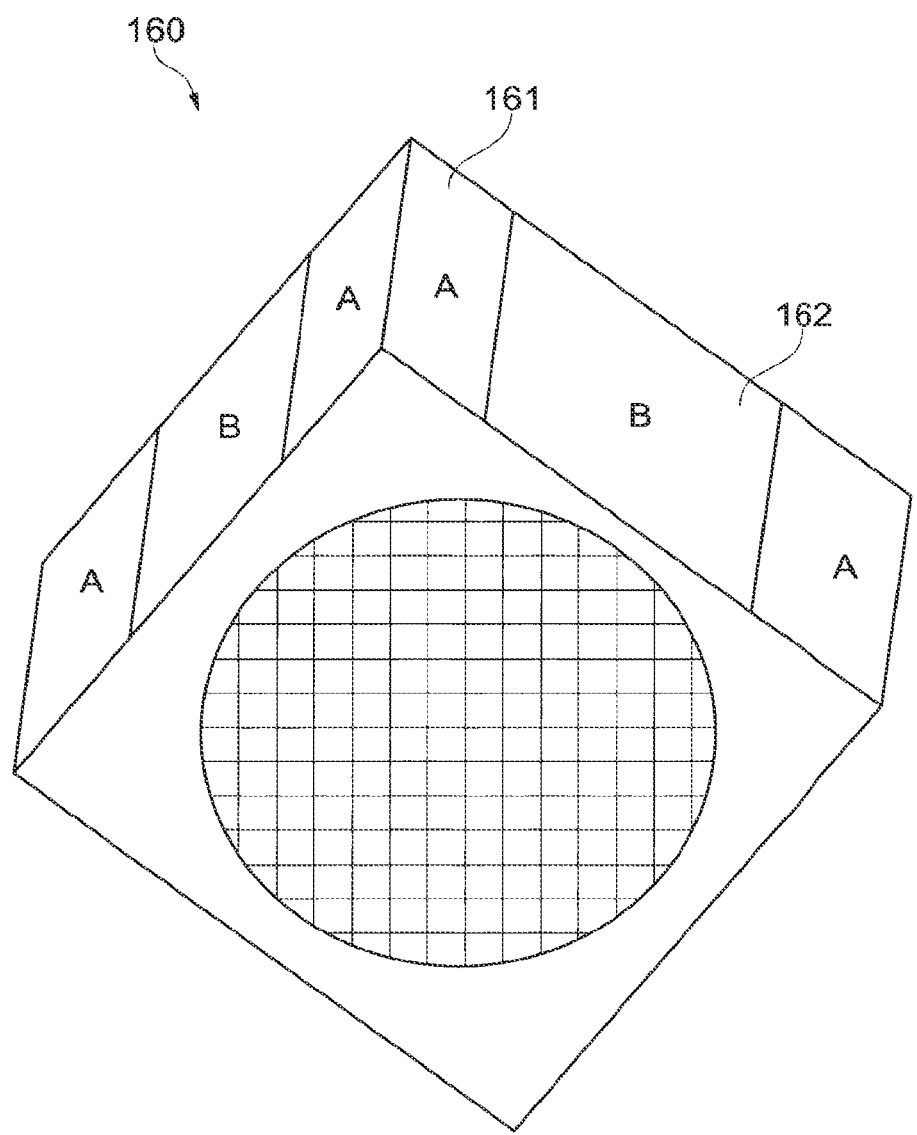
Figure 13:
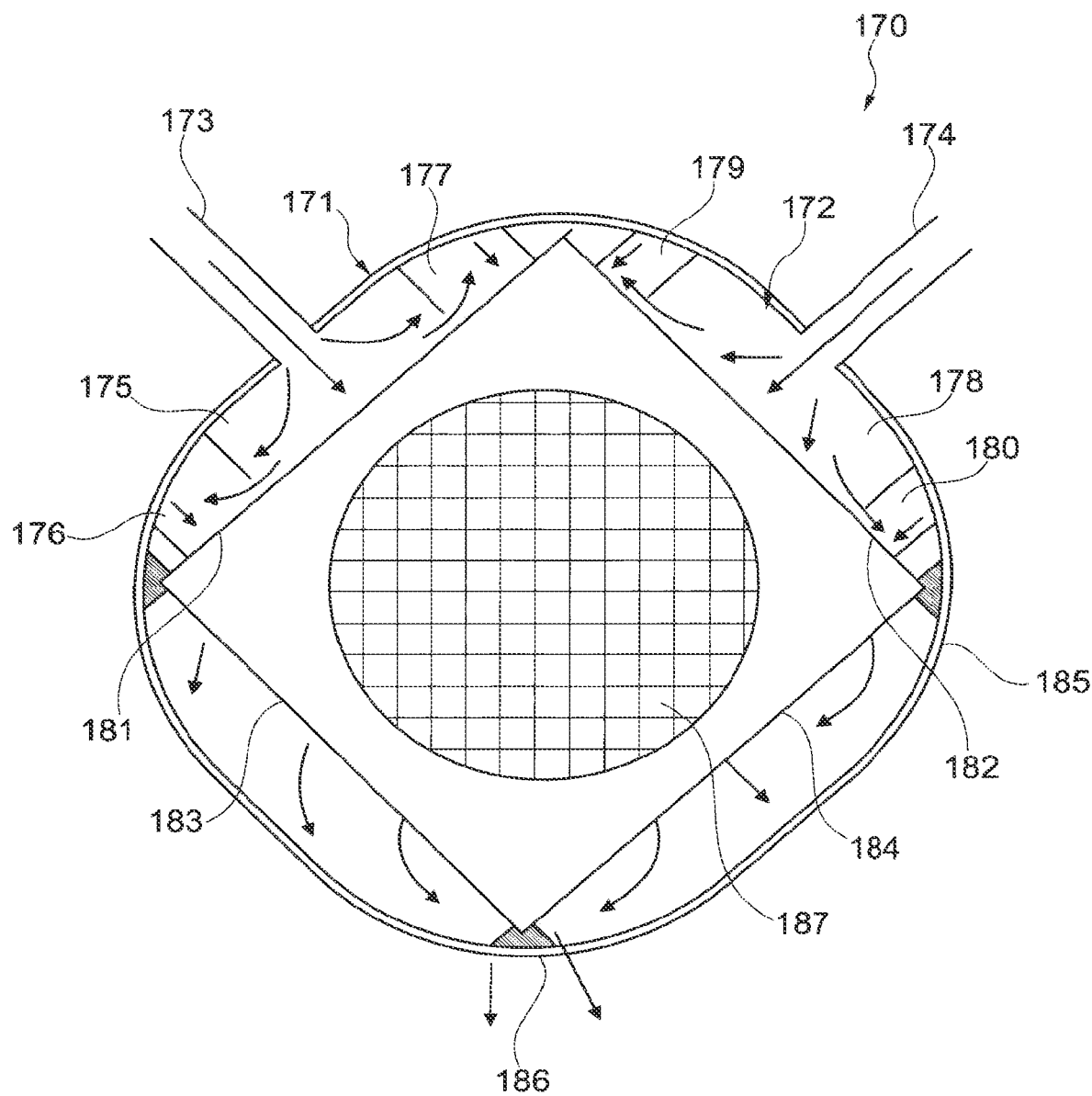
Figure 14:
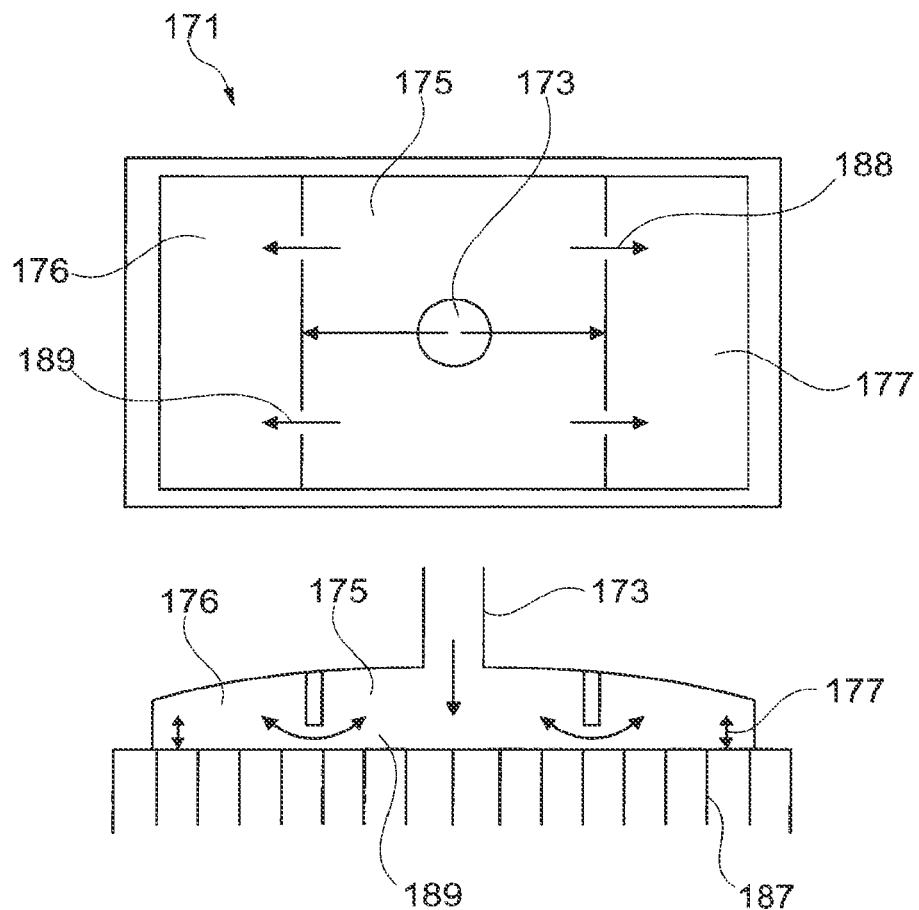
Figure 15:
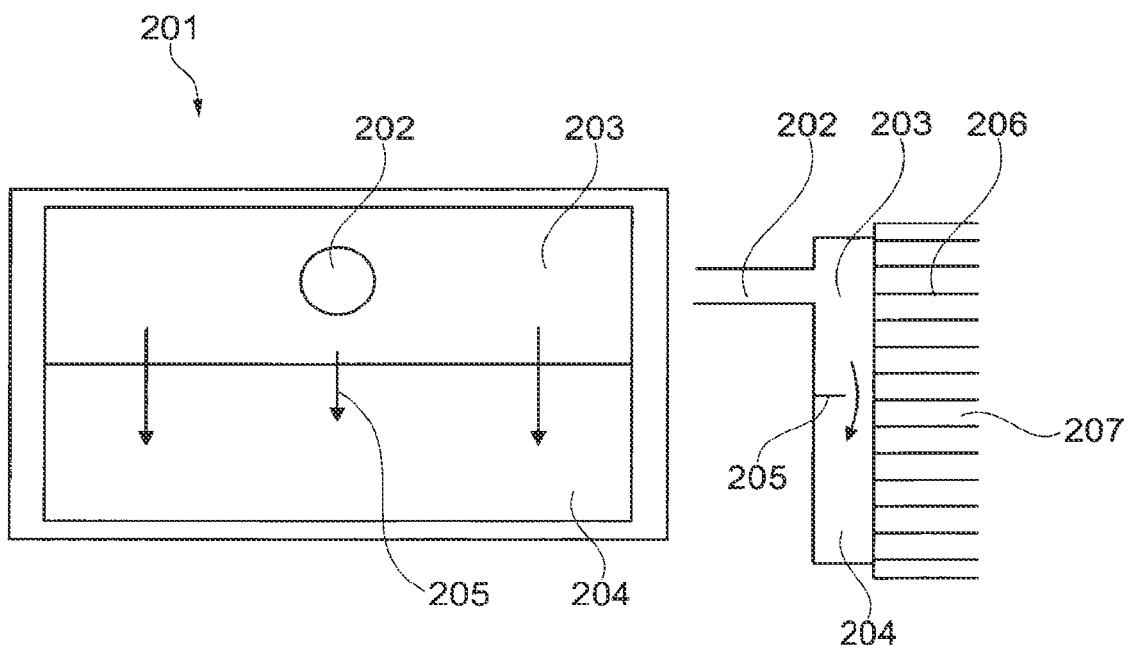
Figure 16:
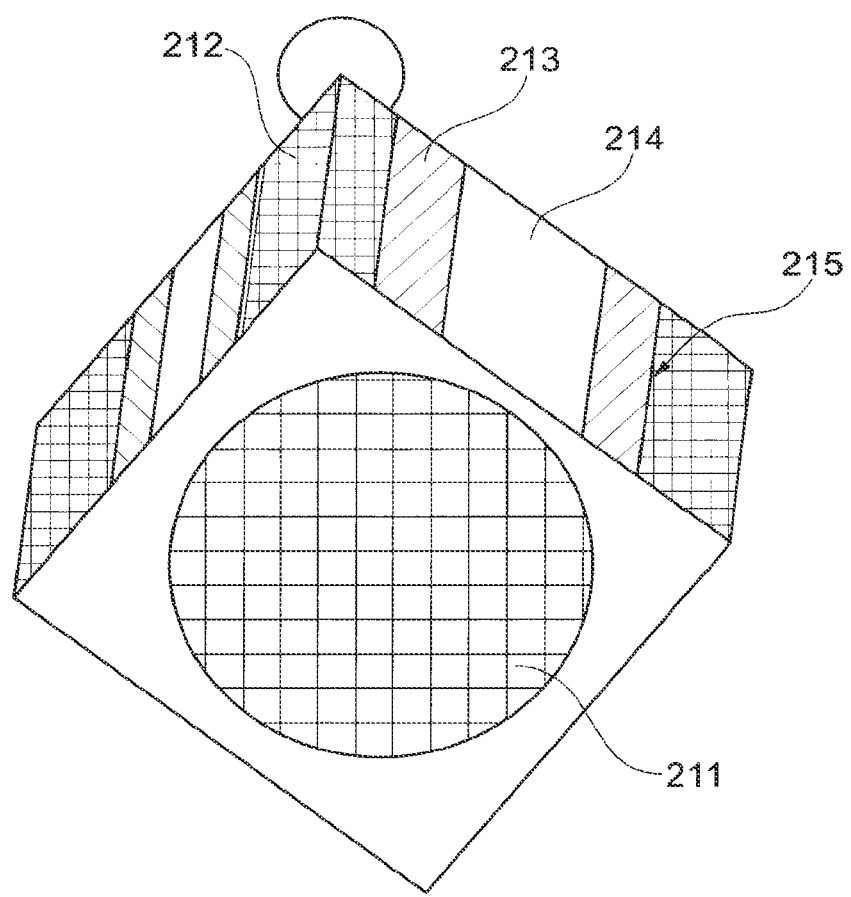
Figure 17:
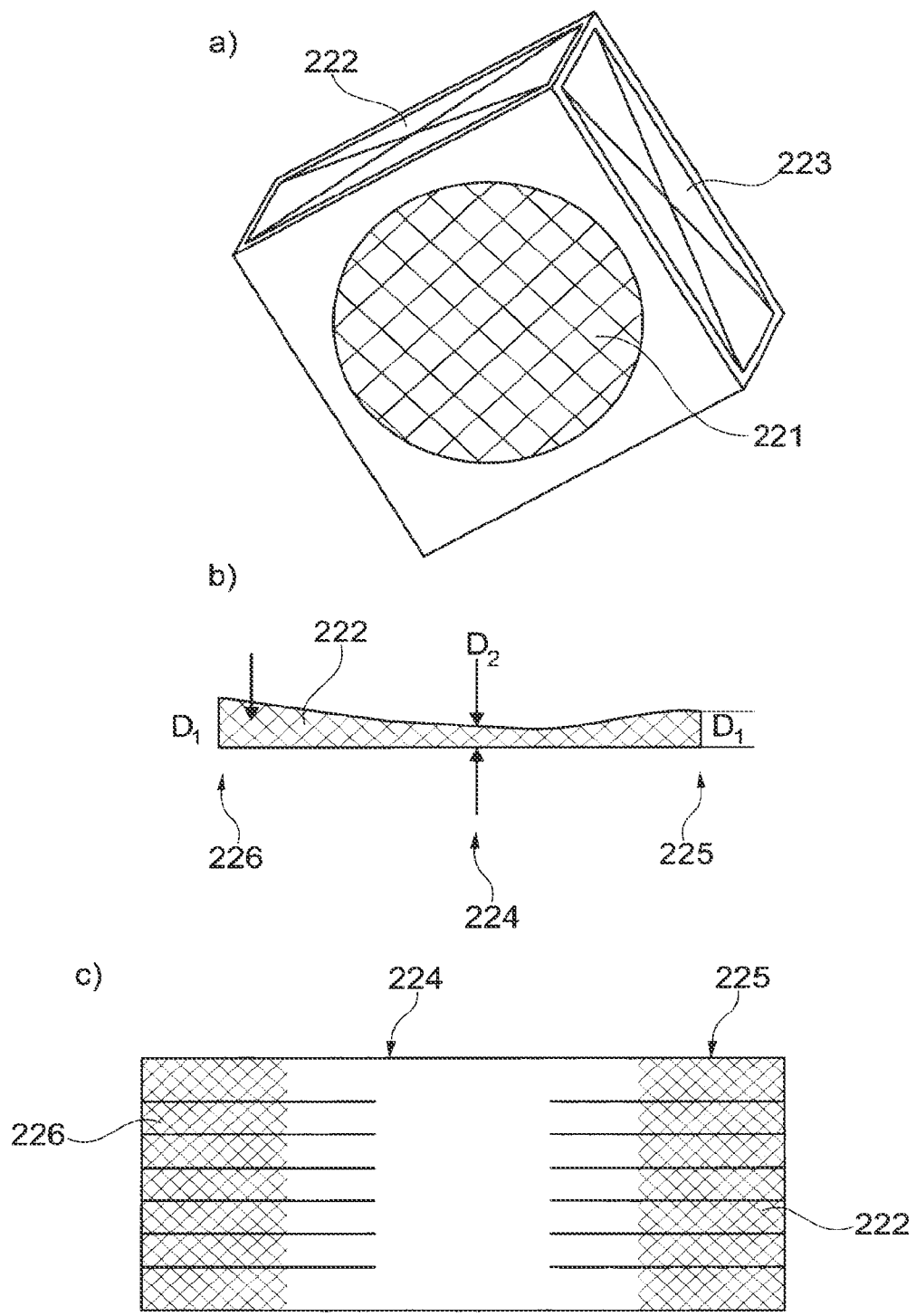
Figure 18:
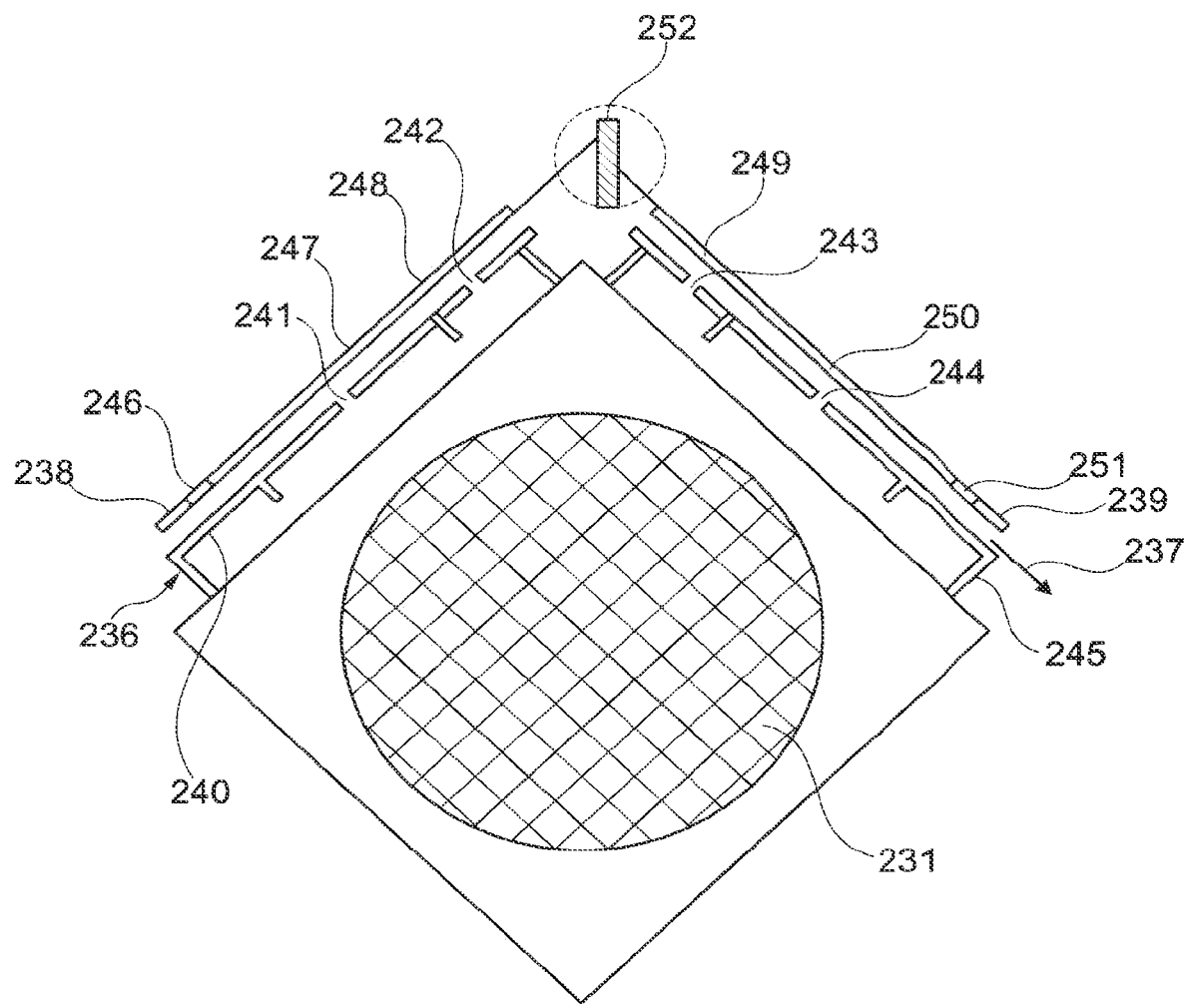
Figure 19:
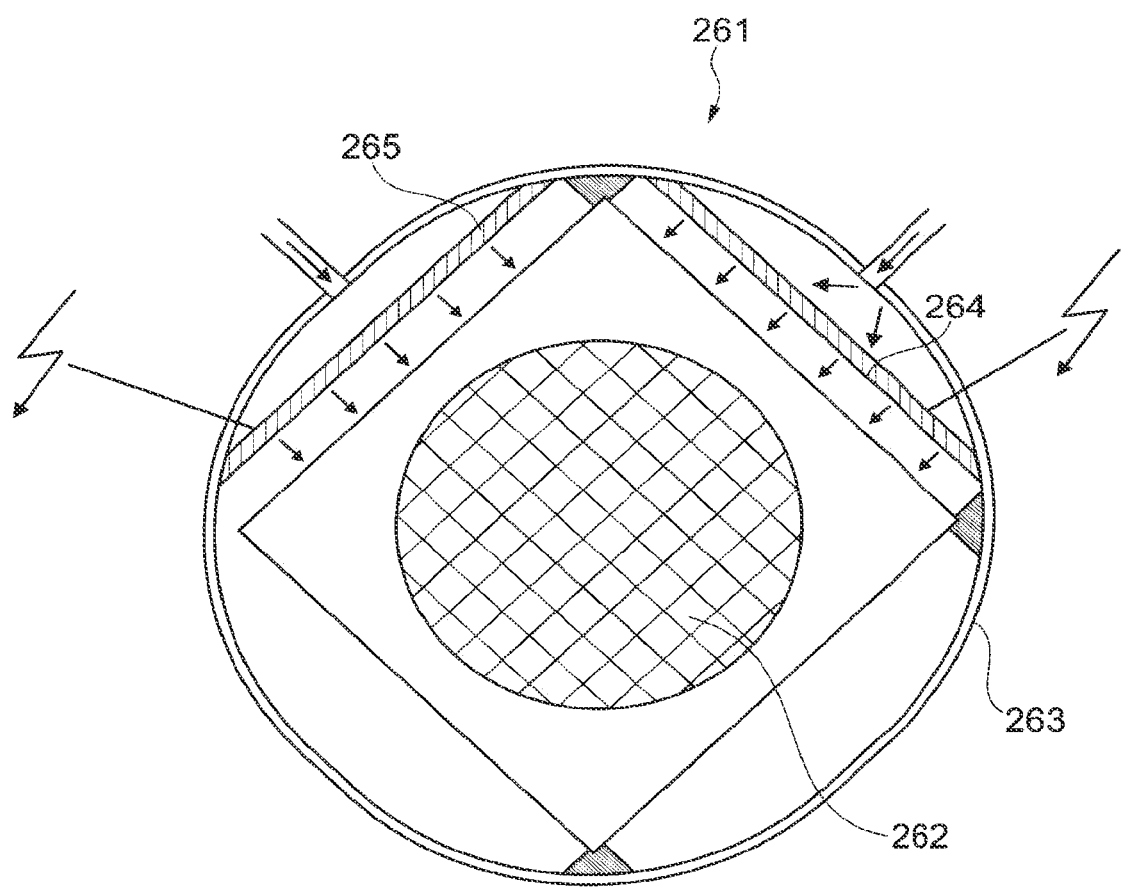
Figure 20:
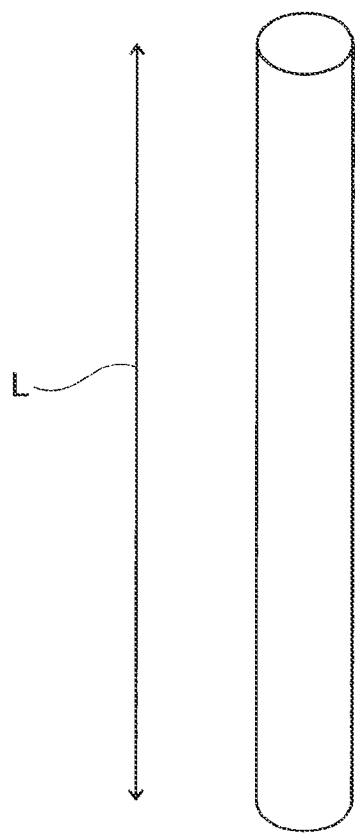

FIG. 5 *a* is a schematic representation of a gas exchange unit with two hollow-fibre modules which are drum-shaped and arranged concentrically one inside the other;

FIG. 5 *b* shows a cross-section from the gas exchange unit in FIG. 5*a*;

FIG. 5 *c* shows a further cross-section of the gas exchange device from FIG. 5*a*, wherein both the air flow direction and the blood flow direction are schematically illustrated;

FIG. 6 is a schematic representation of a gas exchange unit, wherein the hollow-fibre modules are designed as fibre mats;

FIG. 7 *a* is a schematic representation of a gas exchange unit from FIG. 6, wherein the embedding material forms a cylindrical closure towards the blood side;

FIG. 7 *b* is a schematic representation of a fibre arrangement from FIG. 6, wherein the fibre mats are alternately arranged crosswise at an angle of 120° and the embedding material is of cylindrical design towards the blood side;

FIG. 8 *a* is a schematic representation of a plan view of a gas exchange unit in which the hollow-fibre modules are drum-shaped and arranged concentrically one inside the other, and an impermeable layer is used to guide the blood;

FIG. 8 *b* is a schematic representation of a likewise drum-shaped hollow-fibre module arrangement, wherein a plurality of channels is formed by an impermeable layer;

FIG. 9 *a* is a schematic representation of a gas exchange unit, wherein some of the gas exchanger fibres can be continuously switched on or off;

FIG. 9 *b* is a schematic representation of a valve for connection and disconnection;

FIG. 10 is a schematic representation of a gas exchange unit, wherein the diameter-to-length ratio of the hollow fibres>1 (is greater than 1);

FIG. 11 is a schematic representation of a gas exchange unit with two hollow-fibre modules which are formed as fibre mats and arranged one behind the other;

FIG. 12 is a schematic representation of a gas exchange unit formed as a fibre mat, with fibre regions arranged side by side;

FIG. 13 is a schematic representation of a gas exchange unit with an overflow channel device;

FIG. 14 is a schematic representation of the arrangement of the inlet to the overflow channel device in an arrangement according to FIG. 12 in side view in FIG. 14*a*) and in the section of a cross-section in FIG. 14*b*);

FIG. 15 is a schematic representation of the arrangement of the inlet to the overflow channel device in an arrangement according to FIG. 11 in side view in FIG. 15*a*) and in the section of a cross-section in FIG. 15*b*);

FIG. 16 is a schematic representation of a gas exchange unit with various overlays for increasing the pneumatic resistance;

FIG. 17 is a schematic representation of a gas exchange unit with an overlay of differing thickness for increasing the pneumatic resistance in FIG. 17*a*), with a side view of the overlay in FIG. 17*b*) and a plan view of the overlay in FIG. 17*c*);

FIG. 18 is a schematic representation of a gas exchange unit with adjustable overflow channels;

FIG. 19 is a schematic representation of a gas exchange unit with an electric heating element;

FIG. 20 is a schematic representation of a hollow fibre with information on the geometric definition.

Figure 1:
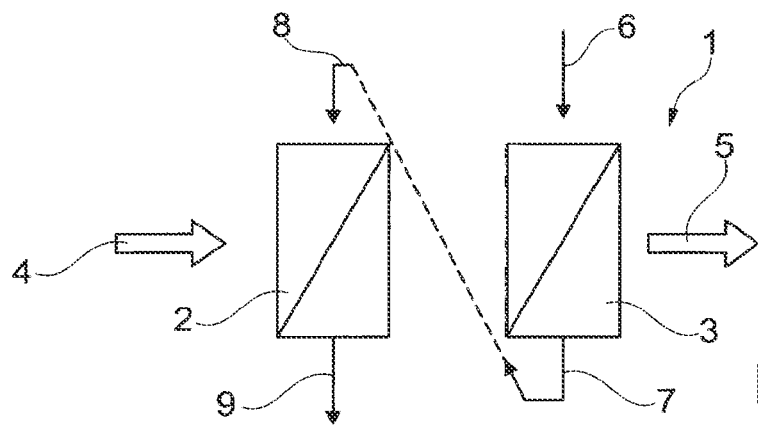
Figure 2:
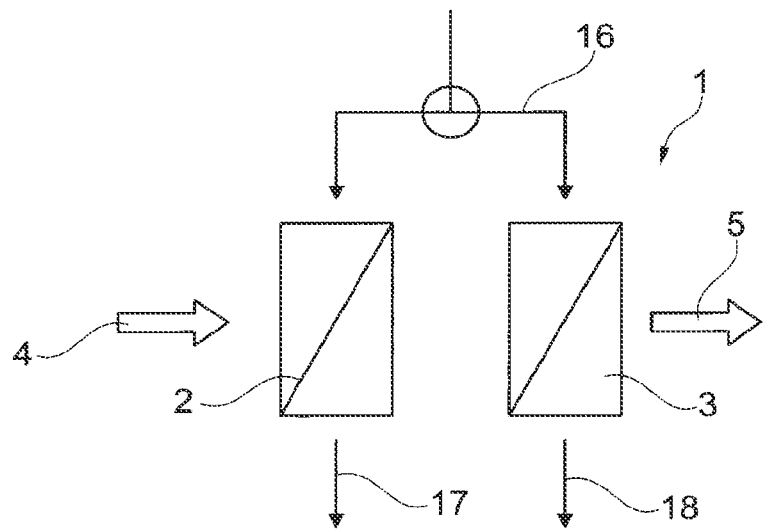
FIG. 2 is a schematic representation of a gas exchange unit with two hollow-fibre modules connected in parallel.

In a gas exchange unit 1 the blood is oxygenated and $CO_2$ depleted from the blood. For this purpose, the blood flows through a hollow-fibre module. Gas flows through the interior of the hollow fibres (not illustrated). In FIG. 1 blood flows through two such hollow-fibre modules 2, 3 sequentially or in series. Here the blood, schematically represented by the arrow 4, first flows into gas exchange unit 2, through this and then gas exchange unit 3, until it is finally schematically represented leaving gas exchange unit 1 by the arrow 5. Once the gas, the flow of which is schematically represented by the arrows 6, 7, 8 and 9, has left the first gas exchanger, it is passed to the second one. As an option gas can also flow through both gas exchangers in parallel, as shown in FIG. 2. It is thus possible to adapt the gas exchange characteristics to suit requirements. This can be done in production during preassembly, prior to use or during use. Here the gas flow is schematically illustrated by the arrows 16, 17 and 18.

Figure 3:
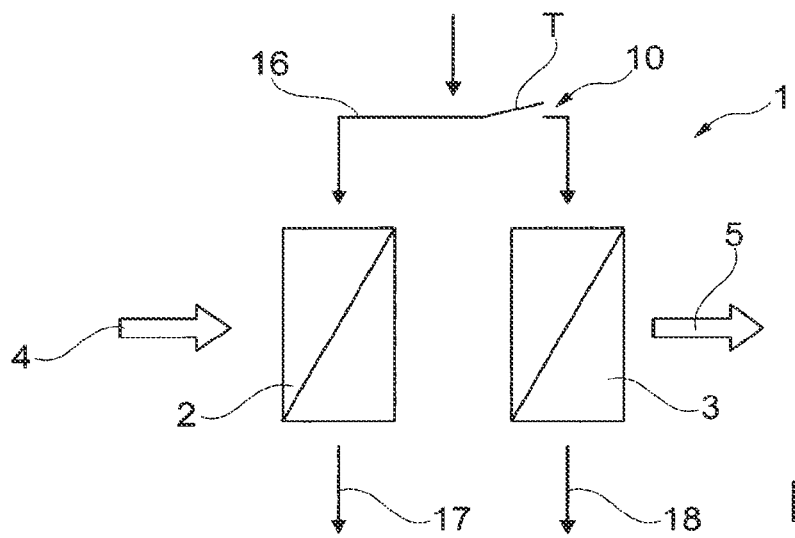
FIG. 3 is a schematic representation of a gas exchange unit with two hollow-fibre modules, one of which can be switched on or off.

As shown in FIG. 1, a counterflow of blood and gas direction is possible, with the blood first flowing through hollow-fibre module 2 and then hollow-fibre module 3, and the gas first flowing through hollow fibre module 3 and then hollow fibre module 2 (so-called countercurrent principle). The reverse order is also possible, in which case the blood first flows through hollow-fibre module 2 and then hollow-fibre module 3, and the gas likewise first flows through hollow-fibre module 2 and then hollow-fibre module 3 (so-called direct current principle). In particular it is possible to switch between the two circuits—in series or in parallel—as required. As shown in FIG. 3, it is also possible to connect or disconnect one of the two hollow-fibre modules. For this purpose, it is connected with a valve 10.

Figure 4:
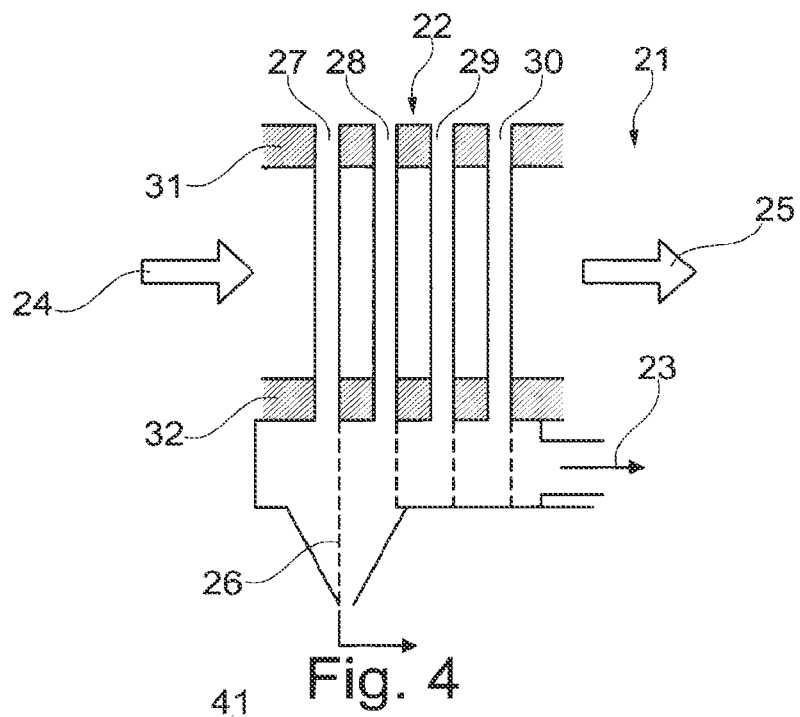
FIG. 4 is a schematic representation of the operating principle of the heat exchange in a hollow-fibre module with a humidifying and heating device connected upstream on the gas side.

The mode of operation of a humidifying and heating device connected upstream on the gas side will be explained below with the aid of the section from a hollow-fibre module 21 as shown in FIG. 4. In this arrangement the heated gas and water vapour flows through the hollow-fibre module 21. The gas flow is represented symbolically by the arrows 22 and 23. The blood flow is represented symbolically by the arrows 24 and 25. The hollow fibres 27, 28, 29 and 30 are fixed in two layers 31 and 32 of embedding material. The gas is saturated with water vapour and has a temperature above blood temperature. In the hollow-fibre module 21 the gas gives off heat to the blood and a part of the water vapour condenses, also releasing the condensation energy to the blood. The condensate 26 is collected beneath the hollow-fibre module 21. The latter therefore functions both as a gas exchanger and heat exchanger.

In the case of the gas exchange unit 41 two hollow-fibre modules 42, 43 are drum-shaped and concentrically arranged one inside the other. They are separated from each other by a separation layer 44, which can also be configured as a grid or mesh. The blood flows outwards from inside as symbolised by the arrows 45 and 46. It is also possible to guide the blood inwards from outside or diagonally outwards as symbolised by the arrows 45, 46, and 47. A possible gas flow path is again symbolised by the arrows 48, 49 and 50. Here first the outer hollow-fibre module 43 is charged with gas and then, in series connection, the inner hollow-fibre module 42. A parallel connection is also possible here. On the whole a gas exchange unit as formed in FIGS. 5 *a*, 5 *b* and 5 *c* is represented as a drum-shaped body.

In a gas exchange unit 61 a stacked arrangement of hollow-fibre modules 62 and 63 may also be selected, as shown in FIG. 6. There the hollow-fibre modules 62, 63 are formed as fibre mats. These can each be arranged alternately crosswise to each other. The gas is symbolised by the arrows 66, 67 and 68, each passed from two sides through the hollow fibre. The blood flows through the gas exchange unit 61, as symbolised by the arrows 64, 65. Two or more of these units may be combined and charged with gas as shown in FIGS. 1 to 3.

In FIG. 7*a* the fibre arrangement from FIG. 6 is designed so that the embedding material 79 around the fibre mats, for example 78, forms a cylindrical closure 80 towards the blood side. In the gas exchange unit 81 in FIG. 7*b* the fibre mats 82 and 83 are arranged crosswise at an angle of 120°. Here the embedding material towards the blood side is also executed with a cylindrical closure 89. The outside, however, is not square compared to FIG. 7a, but hexagonal in design. The blood flow is symbolised by the arrows 84 and 85, with the gas inflow being symbolised by the arrows 86, 86' and 86" and the gas outflow by the arrows 87, 87' and 87". The individual hollow fibres 88 are visible.

In a drum-shaped fibre arrangement 91, 101 as shown in FIG. 8 *a* and *b*, the blood is passed spirally from inside to outside by a blood-impermeable layer 92, 102, 103, 104. Here, as in arrangement 91, a channel is possible in the gas exchange unit 101, or even two or more channels, as in this instance three channels. Here the blood inflow is symbolised by the arrows 93, 105, 106, 107, the blood outflow by the arrows 94, 108, 109, 110.

In the gas exchange unit 121 in FIG. 9a some of the gas exchange fibres such as 122 can continuously be switched on or off as required by an appropriate valve arrangement 123, and thus adapted to meet the need. Two perforated plates 132 and 133 movable relative to each other may be used as a valve 131, for example as shown in FIG. 9 *b*. The blood flow is symbolised by the arrows 124 and 125, the gas flow by the arrows 126, 127 and 128.

As shown in FIG. 10, it is particularly advantageous if the gas exchange unit and the arrangement of the gas exchanger fibres are selected so that the internal diameter of the blood-carrying region is larger than the length thereof. The blood flow is again symbolised by the arrow 144, the gas flow by the arrow 145.

The gas exchange unit 150 in FIG. 11 has two hollow-fibre modules, module A 151 and module B 152, which are formed as fibre mats and are arranged one behind the other. A longitudinal distribution of the gas exchange unit 150 is thus achieved.

The gas exchange unit 160, which is formed as a fibre mat, also has two hollow-fibre regions, region A 161 and region B 162 as shown in FIG. 12, but which are arranged side by side. A transverse distribution of the gas exchange unit 160 is thus achieved.

As shown in FIG. 13, a different charging of hollow-fibre module 170 can then be performed by overflow channel devices 171 and 172. The inflow of the gas takes place through the inlets 173, 174, each of which has a central chamber 175, 178 as well as two side chambers 176, 177 and 179, 180. The gas flows from the central chamber 175, 178 into the two side chambers 176, 177 and 179, 180. This results in an increased charging of sides 181 and 182 of the gas exchange unit 170 in the region of the central chamber 175, 178 as well as a weaker charging in the region of the two side chambers 176, 177 and 179, 180. A different flow through regions A and B is thereby achieved, as shown in FIG. 12. The gas again leaves the fibre bundle 187 at sides 183 and 184 and is led outside through the outlet 186.

This arrangement according to FIG. 12 of the inlet 173 to the central chamber 175 with the side chambers 176, 177 in an arrangement can also be seen in side view in FIG. 14a) and in the section of a cross-section in FIG. 14b). Here it becomes clear how the central chamber 175 is connected to the side chambers 176, 177 by overflow channels such as 188 or 189.

Also, in an arrangement according to FIG. 11, with a charging of the hollow-fibre modules 206, 207 by the overflow channel device 201 a different charging of the hollow-fibre modules A 206 and B 207 becomes possible. This can clearly be seen in FIG. 15 in an arrangement in side view in FIG. 15a) and in the section of a cross-section in FIG. 15b). The overflow channel device 201 has an inlet 202 which introduces the gas into a first chamber 203, whence it is passed into a second chamber 204 through overflow channels such as 205. This results in different charging of the gas exchange unit in the regions of the two chambers 203, 204 in the region of the different hollow-fibre modules A 206 and B 207.

Another possibility for the different charging of the hollow fibre regions A and B in an assembly according to FIG. 12 is the application of an overlay on the fibre bundle 211, as shown in FIG. 16. Here different overlays, overlay A 212, overlay B 213 are applied on a side surface 215, thereby increasing the pneumatic resistance. The central region 214 remains foil-free. This also results in different charging of the three areas here (fibre region A in the region of the overlay A 212, fibre region B 213 in the region of the overlay B and fibre region C (here in addition to the assembly in FIG. 12) in the foil-free central region 214.

A further possibility for the different charging of fibre regions A and B in an assembly according to FIG. 12 is the application of an overlay 222, 223 of differing thickness to increase the pneumatic resistance, as shown in FIG. 16. In FIG. 17a) in a side view of the overlay 222 in FIG. 17b) and a plan view of the overlay in FIG. 17c), each of the regions of differing thickness 225, 226 can be seen as thickness D1 and 224 as thickness D2. Overlay 222 is an air-permeable structure such as a fleece. A different gas permeability is achieved by the different thickness, resulting in a different flow resistance. A different gas permeability is also achieved by a different charging in the flow through the module. A continuous charging gradient can be achieved by a continuous configuration.

One possibility for a structure for the variable charging of a fibre bundle 231 is implemented by adjustable overflow channels 232, 233, 234, 235, as shown in FIG. 18. Here a slide valve 238, 239 is fitted to the overflow channel device 236, 237, by means of which the openings 240, 241, 242, 243, 244, 245 of the overflow channel 236, 237 can be completely or partially covered. For this purpose, the openings 246, 247, 248, 249, 250, 251 of the slide valve 236, 238 are made to coincide completely or partially with those of the overflow channel 240, 241, 242, 243, 244, 245 by means of an adjusting device 252. Thus, the gas can either completely or partially enter directly into the chambers of the overflow channel or flow on into the chambers by way of the overflow channels 232, 233, 234, 235.

In a gas exchange unit 261 with a fibre bundle 262, an electric heating element 264 may be arranged in the housing 263 to prevent condensation.

For the individual hollow fibre, it is advantageous if, as shown schematically in FIG. 20, the fibre length (L1) relative to the internal fibre diameter (Di) is less than 500. In particular the length (L1) may be less than 80 mm, the internal fibre diameter (Di) may be in the order of 160 to 200 μm.

The invention claimed is:

1. A Gas exchange unit with a hollow-fibre module, characterised in that a gas flow characteristic of the hollow-fibre module is adaptable,
   wherein an overflow device is provided on the hollow-fibre module to allow different charging of fibre regions by means of differing pressure gradients,
   wherein the overflow device provides a plurality of gas-chambers connected together by gas-overflow-channels,
   wherein in addition to the overflow device an overlay is applied directly on a fibre bundle of a side surface of the hollow-fibre module,
   wherein the overlay is different from the overflow device; and wherein the overlay has a continuous pneumatic resistance gradient to increase the pneumatic resistance.

2. The gas exchange unit according to claim 1, characterised in that the hollow-fibre module is completely or partially connectable to or disconnectable from the gas flow.

3. The gas exchange unit according to claim 1, characterised in that on a gas side, said gas exchange unit has a shutter configured to regulate an amount of gas flow to the different fibre regions.

4. A Gas exchange unit according to claim 1, characterised in that the fibre regions of the hollow-fibre module can be differently charged with gas.

5. The gas exchange unit according to claim 1, characterised in that said gas exchange unit has a cover.

6. The gas exchange unit according to claim 5, characterised in that the cover has a pneumatic resistance gradient.

7. The gas exchange unit according to claim 1, characterised in that a gas-side humidifying and heating device is connected upstream of the hollow-fibre module.

8. The gas exchange unit according to claim 1, characterised in that the hollow-fibre module is drum-shaped.

9. The gas exchange unit according to claim 1, characterised in that in the hollow-fibre module a blood-impermeable layer is spirally arranged from an inside of a spiral to an outside of the spiral.

10. The gas exchange unit according to claim 1, characterised in that a blood flow can be guided from a peripheral region of the hollow-fibre module to a more central region of the hollow-fibre module or from the more central region to the peripheral region or diagonally between the peripheral region and the more central region of the hollow-fibre module.

11. The gas exchange unit according to claim 1, characterised in that said gas exchange unit has two or more hollow-fibre modules.

12. The gas exchange unit according to claim 11, characterised in that the hollow-fibre modules can be differently charged with gas.

13. The gas exchange unit according to claim 11, characterised in that said gas exchange unit has a second overflow device.

14. The gas exchange unit according to claim 11, characterised in that the hollow-fibre modules are connected with a valve.

15. The gas exchange unit according to claim 11, characterised in that the hollow-fibre modules configured to guide a gas flow can be connected in parallel or in series.

16. The gas exchange unit according to claim 11, characterised in that the hollow-fibre modules are drum-shaped and concentrically arranged one inside the other.

17. The gas exchange unit according to claim 11, characterised in that the hollow-fibre modules are formed as fibre mats and arranged one behind the other.

18. The gas exchange unit according to claim 17, characterised in that a fibre direction of a fibre mat is arranged at an angle to a fibre direction of a second fibre mat.

19. The gas exchange unit according to claim 18, characterised in that the angle is between 10° and 170°.

20. The gas exchange unit according to claim 1, characterised in that a diameter to length ratio of the hollow-fibre module is less than 2.

21. The gas exchange unit according to claim 1, characterised in that it has an electric heating element.

22. The gas exchange unit according to claim 21, characterised in that it has a heating element provided on the gas side.

23. The gas exchange unit according to claim 1, characterised in that an embedding material forms a cylindrical closure towards the blood side.

24. A Kit with the gas exchange unit, according to claim 1, and a humidifying and heating device, characterised in that the humidifying and heating device is upstream of the hollow-fibre module in the gas flow.

25. The Gas exchange unit of claim 1, characterised in that the overflow device further comprises adjustable overflow channels.

26. The Gas exchange unit of claim 1, characterised in that the overlay is comprised at least one of foil or fleece.

* * * * *